US005112574A

United States Patent [19]

Horton

[11] Patent Number: 5,112,574

[45] Date of Patent: May 12, 1992

[54] MULTITITER STOPPER ARRAY FOR MULTITITER PLATE OR TRAY

[75] Inventor: Nikki Horton, Arlington, Va.

[73] Assignee: Imanigation, Ltd., Gaithersburg, Md.

[21] Appl. No.: 691,811

[22] Filed: Apr. 26, 1991

[51] Int. Cl.[5] ........................ B01L 3/00; B01L 11/00; C12M 1/00; C12M 1/18

[52] U.S. Cl. ................................... 422/102; 422/101; 422/104; 435/301; 215/364

[58] Field of Search ............... 435/293, 300, 301, 299, 435/297, 298; 422/101, 104, 102; 215/364

[56] References Cited

U.S. PATENT DOCUMENTS

| | | | |
|---|---|---|---|
| 4,599,314 | 7/1986 | Shami | 435/287 |
| 4,657,867 | 4/1987 | Guhl et al. | 435/284 |
| 4,673,651 | 6/1987 | Rothenberg et al. | 435/301 |

*Primary Examiner*—Jill A. Johnston
*Assistant Examiner*—Long V. Le
*Attorney, Agent, or Firm*—Eric P. Schellin

[57] ABSTRACT

An array of stoppers held in a lid. The stoppers have indentations in their top sides that slide into tracks or recesses in the lid. The lid holds the stoppers so that they may be inserted into the wells of any multititer plate by either hand or machine. The lid has a removable end that allows for the sliding removal of the lid without removing the stoppers from wells that form the multititer plate or tray.

4 Claims, 5 Drawing Sheets

FIG. 1
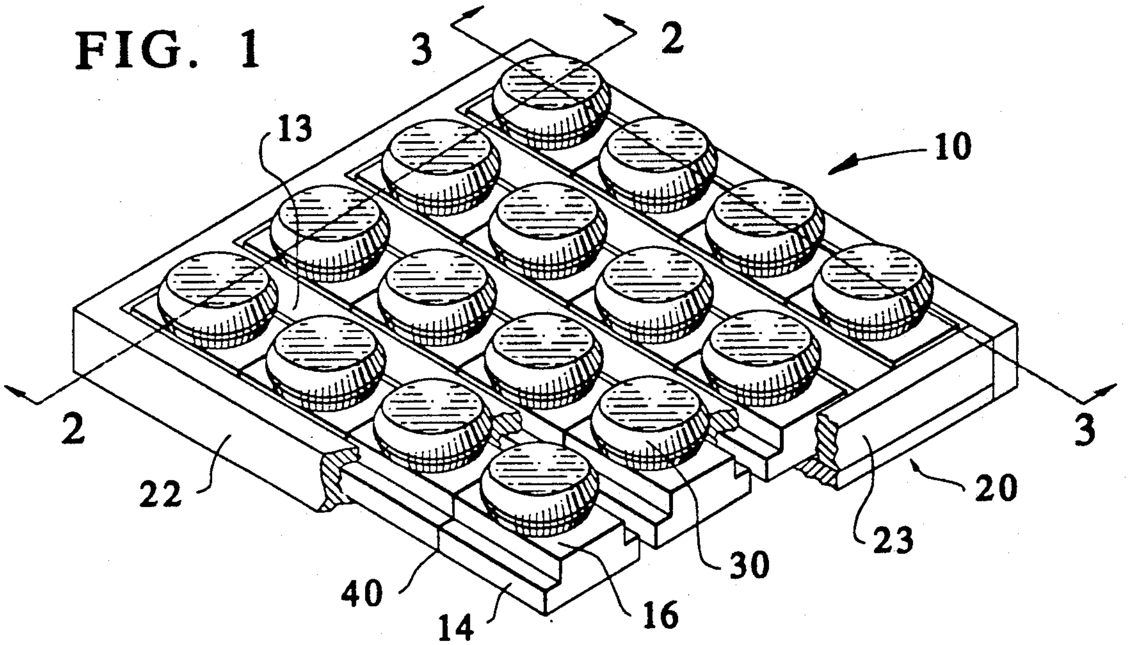
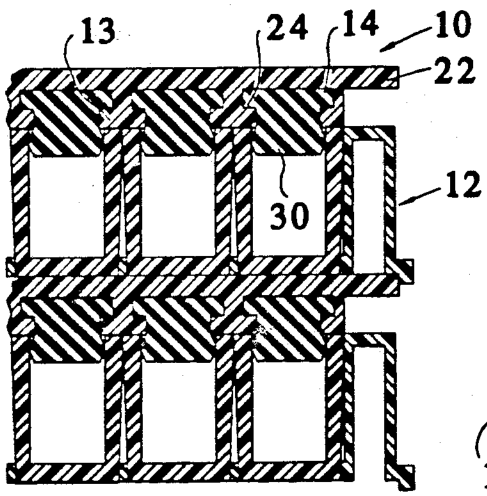
FIG. 2
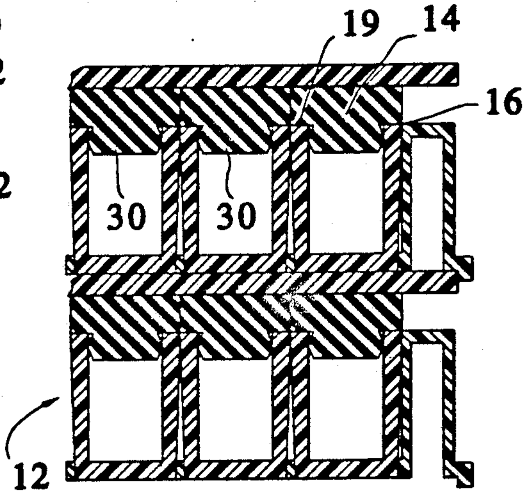
FIG. 3

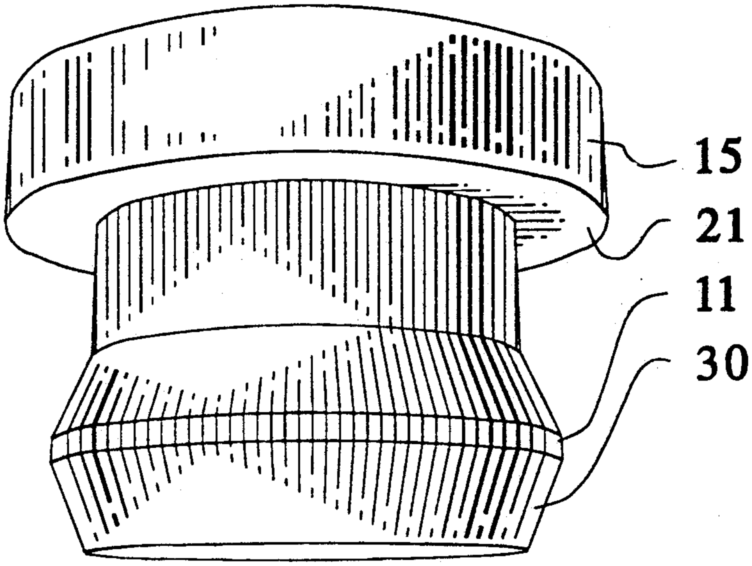
FIG. 4
FIG. 6
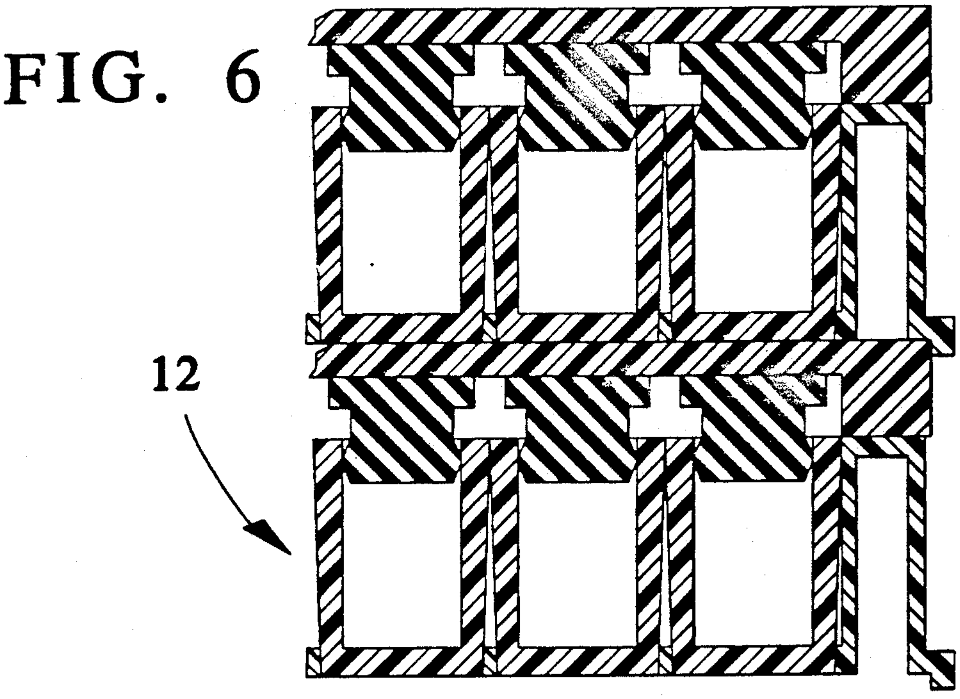

FIG. 5
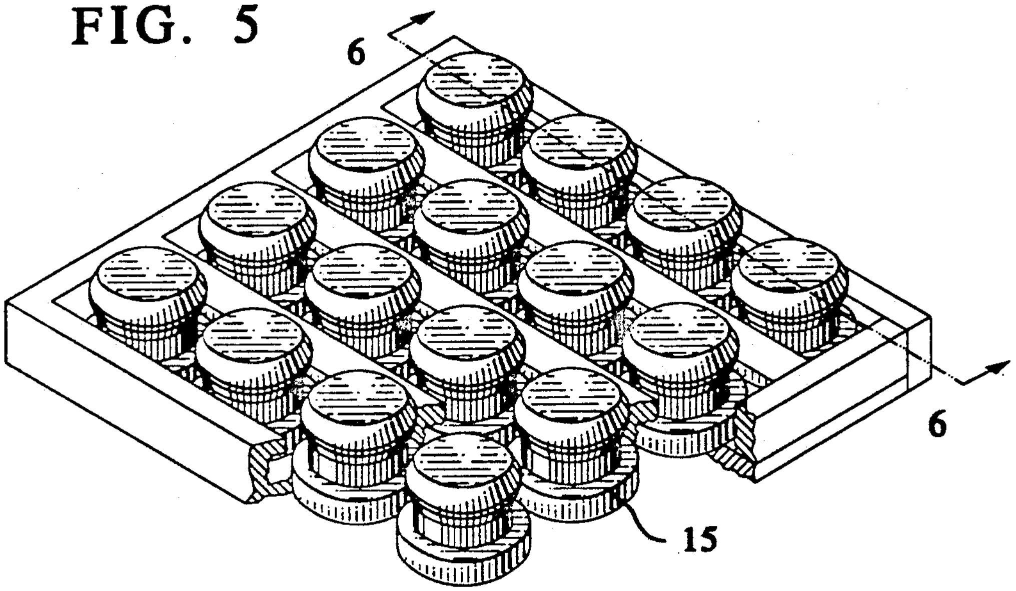
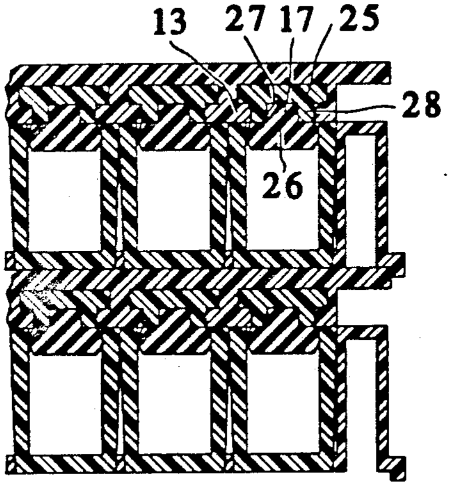
FIG. 7
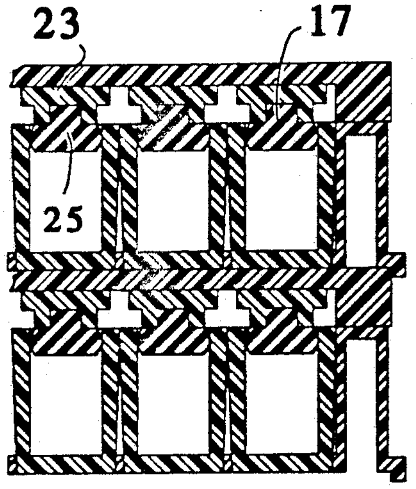
FIG. 8

MULTITITER STOPPER ARRAY FOR MULTITITER PLATE OR TRAY

BACKGROUND OF THE INVENTION

1. FIELD OF THE INVENTION

The invention relates to an array of stoppers held in a common tray or lid. The stoppers have indentations in their top sides by means of which they can slide into tracks provided in the lid. The lid holds the stoppers so that they may be inserted into a conventional multititer plate by either hard or machine. The multititer plate contains rows of upwardly facing open ended tubes or cuvettes. The lid has an end that is removable thereby allows for the sliding removal of the lid without removing the stoppers from the tubes that form the multititer plate or tray. The lid is shaped to allow for stacking of plates and may be reusable. The tubes may be sold with or without a liquid therein so that stoppering is needed as in a traditional full size test tube. More particularly the invention is directed to a multititer stopper array for a conventional multititer plate or tray consisting of integral T-shaped elements defining a generally elongated construction throughout and having a free surface area extending along the side thereof to engage with open tubes or open wells in the tray.

The lid defines a frame having recesses for receiving the T-shaped elements in securement within the frame of the lid. A series of stoppers are integrally disposed on the free surface area of the I-shaped elements, and the series of stoppers extending therefrom to be matingly received in a series of the open cells or wells, and also the method of construction thereof.

The invention relates further to a re&hod of making a multititer stopper array for a multititer plate or tray consisting of the steps of molding a T-shaped means defining a generally elongated construction throughout and having a free surface area extending along a side to engage with open cells or open wells in the tray and having a series of stopper means integrally disposed on the free surface area of the T-shaped means. The series of stopper means extending therefrom to be matingly received in a series of the open cells or wells, and assemblying and securing a lid means defining a frame having recess means for receiving the T-shaped means within the frame of the lid means thereof as more particularly described herein.

2. Description of the Prior Art

A multititer plate is usually developed as an array of about 96 miniature test tubes in a single plate or tray having wells or cells that could be chemically treated and recessed as a single unit. Such an arrangement has a drawback that all the tubes had to be used at the same time. If only one test of the unit was used, the remainder of the plate was wasted, later versions were constructed in holders containing strips of 12, 8 and finally, individual tubes, cells or wells, all still retaining the original dimensions. Normally these tubes are coated inside and dried as a single plate or tray and then sold whole or in smaller groups.

Various prior art multititer stopper array systems, and the like, as well as apparatus and method of their construction in general, are found to be known; and exemplary of the U.S. prior art are the following:

Shami; U.S. Pat. No. 4,599,314

Vince; U.S. Pat. No. 4,877,659

Shami discloses the provision of a tray and a plurality of individual cells in the form of specimen vessels removably located in the tray and a provision of a lid for the tray physically identified with the cells of the tray.

Vince is seen to show the multiwell assay/culture strips of wells arranged in linear and side-by-side relation on a base and the Vince patent cited Shami above as to whether it is obvious to provide a lid for the wells that form a base of the multiwell assay/culture strips of wells.

These patents or known prior uses teach and disclose various types of coverings for multiwell assay/culture strips of various sorts and of various manufactures and the like as well as methods of their construction, but none of them whether taken singly or in combination disclose the specific details of the combination of the invention in such a way as to bear upon the claims of the present invention.

SUMMARY OF THE INVENTION

An advantage and feature of the invention is to provide an array of stoppers held in a common tray or lid, the stoppers having indentations thereby forming tracks proximate and under their top sides. They slide into tracks or recesses in the lid. The lid holds the stoppers so that they may be inserted into any conventional multititer plate by either hand or machine. The lid has an end portion that is removable and thereby allows for the sliding removal of the lid without removing the stoppers from tubes that form the multititer plate or tray. The lid is shaped to allow for stacking of plates and may be reusable.

Another object of the invention is directed to a device providing for multititer stopper array for a multititer plate or tray consisting of an integral T-shaped element defining a generally elongated construction throughout and having a free surface area extending along one side to engage with open cells or open wells in the tray. A lid defining a frame having recesses for receiving the T-shaped element in securement within the frame of the lid and a series of stoppers integrally disposed noncomitantly with the T-shaped elements, and the series of stoppers extending therefrom to be matingly received in a series of the open cells or wells, and also the method of construction thereof.

Also an object of the invention in one embodiment is to provide an integral T-shaped element that is provided with break off or snap off detent disposed between each of the stoppers that allow for the separation of the stoppers from the series of the open cells or wells.

Another object of the invention is to provide a lid that is constructed of thermoplastic material suitable for washing and drying and adapted to be reusable as desired.

These together with other objects and advantages which will become subsequently apparent reside in the details of the process and operation thereof as more fully hereinafter is described and claimed, reference being had to the accompanying drawings forming a part thereof, wherein like numerals refer to like parts throughout.

DESCRIPTION OF THE SEVERAL VIEWS OF DRAWINGS

FIG. 1 is a fragmented perspective view of a lid having a plurality of stoppers for a multititer tray.

FIG. 2 is an inverted partial sectional view taken along lines 2—2 of FIG. 1 and embodying the concepts of the invention;

FIG. 3 is an inverted partial sectional view taken along lines 3—3 of FIG. 1 and embodying the concepts of the invention:

FIG. 4 is a perspective of an enlarged view of one of the embodiments of the stoppers used in the array in the lid;

FIG. 5 is a fragmented perspective view of a lid having a second embodiment of a plurality of stoppers for a multititer tray;

FIG. 6 is an inverted partial sectional view taken along lines 6—6 of FIG. 5.

FIG. 7 is a similar partial sectional view as FIG. 2 with an alternate embodiment for the stopper;

FIG. 8 is similar partial sectional view as FIG. 6 with the alternate embodiment from the stopper;

DESCRIPTION OF THE PREFERRED EMBODIMENTS OF THE INVENTION

Figure 9:
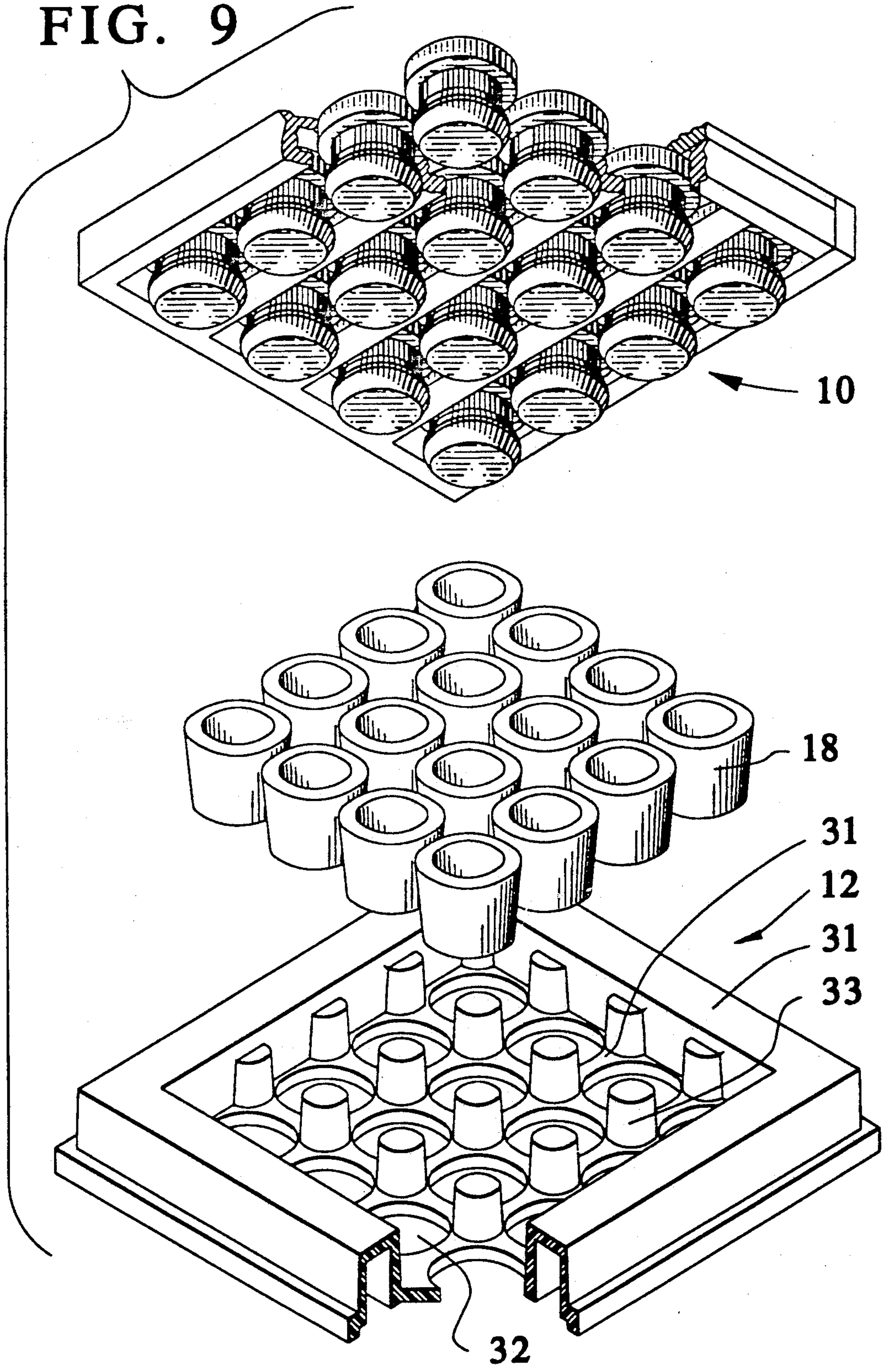
FIG. 9 is a fragmented exploded view of the tray, a plurality of tubes and the lid carrying the stoppers thereabove.

Referring now to the drawings there is shown in the FIG. 1 a multititer stopper array 10 for a multititer plate or tray 12 (See FIG. especially FIG. 9, for instance) having T-shaped element 14 formed of elastomeric material or the like by molding or the like and that defines a generally elongated construction throughout and has a free surface area 16 that extends along a side adapted to interface with open cells or open wells 18 in the tray 12.

A lid 20 defines a frame 22 formed by molding or the like that has a recess 24 that receives the T-shaped element 14 in securement within the frame 22 of the lid 20. A series of stoppers 30 are integrally disposed on the free surface area 16 of the T-shaped element 14 so the series of stoppers 30 extend therefrom for matingly being received in a series of the open cells or wells 18.

In one embodiment, the T-shaped element 14 is provided with break off or snap off along weakened portions 40 disposed between the T-shaped element 14 30 to allow for individual removal of T-shaped elements from the series.

It will be noted that FIGS. 2 and 3 show the lid 20, of the present invention having a plurality of stoppers 30 within the respective mouths of wells 18. Note in FIG. 3 that the surface area 16 sits astride the upwardly facing mouth portion 19 of the well 18.

In FIG. 2 ore can see the elongated tracks 13 or the underside of the lid 20 between which the T-shaped elements 14 are disposed. IN the embodiment of FIG. 1, the T-shaped elements are in an elongated integrally attached strip which are loaded onto the lid as shown. By means of weakened portion 40 individual T-shaped element 14 and the concomitant stopper 30 may be severed from its immediately longitudinal adjacent T-shaped element 14 as desired.

The frame 22 of the lid 20 is provided with a removable end portion 23 which when removed permits the frame to be slid off the titer plate 12 having behind the T-shaped elements 14 and concomitant stoppers 30.

FIG. 4 displays another embodiment of a stopper 15. It will be seen that it is essentially cylindrical and does not have a straight edge portion for strip connections. It does have a shoulder portion 21 which slidably assembles onto tracks 13 as described in the above. This embodiment of the stopper 30 as before has a lower wider portion 11 which is compressed when it is in the well and forms a secure fit therein.

In FIG. 5 one can see the frame 22 having loaded thereinto the embodiment of stopper 15 in a similar fashion as with regard to the T-shaped element 14 and concomitant stopper 30. Except for the fact that the stopper 15 is somewhat different, the frame is the same and the function of the stopper 15 is the same, but the stoppers 15 are not connected to one another.

FIGS. 7 and 8 detail another embodiment of the stopper 17 which has the external appearance of the embodiment shown in FIGS. 4 and 5 but from the cross section shown by FIGS. 7 and 8, it can be seen that the stopper 17 is constructed of two parts and are secured together by mating and gluing therebetween. The upper part 25 is constructed of a harder plastic material having a lower co-efficient of friction than the lower part 26 which is constructed of a more elastomeric material that it stoppers the well fairly securely. The said upper part 25 has a female recess 27 which is detailed to accept male portion 28 of the lower part 26.

For a better understanding of the invention attention is directed to FIG. 9 which is an exploded view of the assembly. The conventional tray 12 has a frame 31 with a bottom 31 having openings 32. In order to retain the wells 18 in spaced secured relationship the bottom is provided with upwardly extending abutments 33 which are dimensioned and spaced whereby the wells when in place cannot pass therebetween. The openings 32 are dimensioned whereby the wells cannot pass therethrough. The wells 18 are conventional cylindrical vessels having a flat bottom. The wells are destined to fit in between the abutments 33.

Positioned in exploded fashion is the stopper array 10 which is destined to fit into the upwardly facing wells when they are seated into tray 12.

Figure 10:
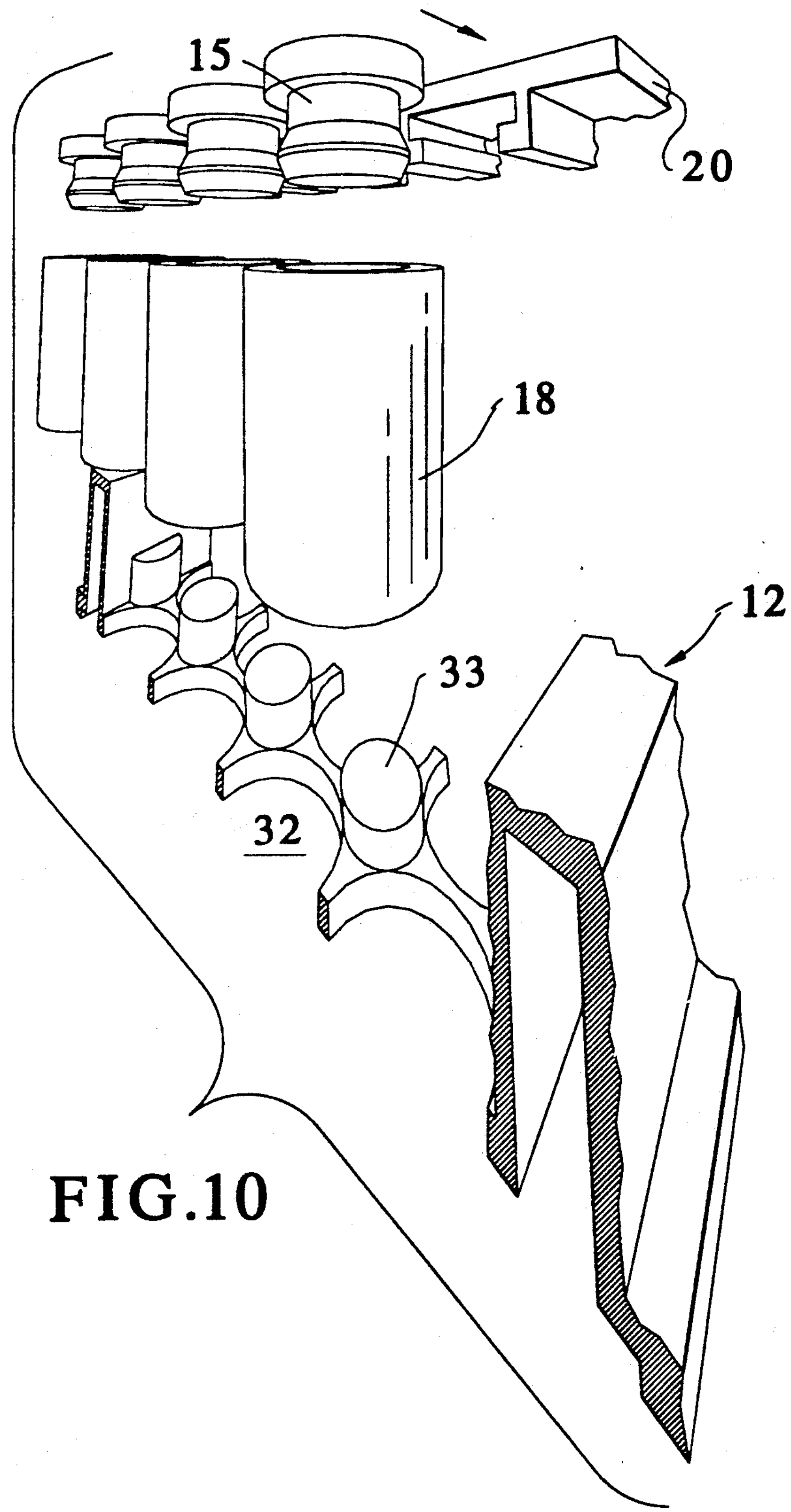
FIG. 10 is another but enlarged fragmented exploded view of a cross section of the tray, a plurality of tubes and the lid in a state of being slidingly removed to thereby release the stoppers.

FIG. 10 is another enlarged more fragmented exploded view to clearly show the stoppers 15 being released as the lid 20 is withdrawn.

The lid 20 is constructed of thermoplastic material suitable for washing and drying and adapted to be reusable.

The apparatus of the multititer stopper array 20 for multititer plates or trays 12 of the invention may be so constructed and arranged in its component parts that it may be assembled as a kit or in kit form.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed and desired to be secured by Letters Patent is:

1. Multititer stopper array for multititer plate or tray comprising

T-shaped means defining a generally elongated construction throughout and having a free surface area extending along a bottom side to engage with open cells or open wells in the tray, lid means defining a frame having a plurality of recess means for slidingly receiving the T-shaped means in securement within the frame of the lid means, a series of stopper means integrally disposed on the free surface area of the T-shaped means, and the series of stopper means extending from said free surface area to be matingly received in a series of the open cells or open wells.

2. The apparatus of claim 1 wherein the T-shaped means is provided with break off or snap off weakened portion disposed between each of the stopper means that allow for removing each of the stopper means from the series of the stopper means.

3. The apparatus of claim 1 wherein the lid means is constructed to include end removable means whereby the lid means slid from the series of stopper means while leaving said series of stopper means in sealing relationship with said open cells or open wells.

4. The apparatus of claim 1 wherein the lid means is constructed of a thermoplastic material means suitable for washing and drying and adapted to be reusable.

* * * * *